United States Patent [19]

Dennison

[11] Patent Number: 5,476,665
[45] Date of Patent: Dec. 19, 1995

[54] AZLACTONE FUNCTIONAL PARTICLES INCORPORATED IN A MEMBRANE FORMED BY SOLVENT PHASE INVERSION

[75] Inventor: Kathleen A. Dennison, Grant Township, Washington County, Minn.

[73] Assignee: Minnesota Mining and Manufacturing Company, St. Paul, Minn.

[21] Appl. No.: 227,261

[22] Filed: Apr. 13, 1994

[51] Int. Cl.$^6$ .............................. A61K 9/26; A61K 9/00; A61K 31/785; C08J 5/20

[52] U.S. Cl. ................... 424/484; 424/485; 424/486; 424/487; 424/488; 424/78.3; 424/194.1; 514/772.1; 521/27; 523/336

[58] Field of Search ....................... 424/78.1, 78.3, 424/484, 486, 488; 521/25, 27; 514/772.1; 525/206; 523/336

[56] References Cited

U.S. PATENT DOCUMENTS

| | | | |
|---|---|---|---|
| 3,488,327 | 1/1970 | Kollinsky et al. | 260/78.3 |
| 3,583,950 | 6/1971 | Kollinsky et al. | 260/78 |
| 3,598,790 | 8/1971 | Kollinsky et al. | 260/78.3 |
| 3,634,218 | 1/1972 | Gotohda et al. | 204/159.17 |
| 3,941,718 | 3/1976 | Barabas et al. | 252/430 |
| 3,971,373 | 7/1976 | Braun | 128/146.2 |
| 4,045,353 | 8/1977 | Kosaka et al. | 210/502 |
| 4,153,661 | 5/1979 | Ree et al. | 264/120 |
| 4,280,970 | 7/1981 | Kesting | 264/1.7 |
| 4,304,705 | 12/1981 | Heilmann et al. | 260/30.4 |
| 4,340,479 | 7/1982 | Pall | 210/490 |
| 4,373,519 | 2/1983 | Errede et al. | 128/156 |
| 4,407,846 | 10/1983 | Machi et al. | 427/35 |
| 4,451,619 | 5/1984 | Heilmann et al. | 525/379 |
| 4,485,236 | 11/1984 | Rasmussen et al. | 544/69 |
| 4,563,388 | 1/1986 | Bonk et al. | 428/304.4 |
| 4,565,663 | 1/1986 | Errede et al. | 264/120 |
| 4,595,726 | 6/1986 | Klosiewicz | 525/71 |
| 4,605,685 | 8/1986 | Momose et al. | 522/124 |
| 4,613,665 | 9/1986 | Larm | 536/20 |
| 4,693,985 | 9/1987 | Degen et al. | 436/531 |
| 4,695,608 | 9/1987 | Engler et al. | 525/308 |
| 4,705,753 | 11/1987 | Gregor et al. | 435/180 |
| 4,722,898 | 2/1988 | Errede et al. | 435/182 |
| 4,726,989 | 2/1988 | Mrozinski | 428/315.5 |
| 4,737,560 | 4/1988 | Heilmann et al. | 526/304 |
| 4,777,276 | 10/1988 | Rasmussen et al. | 556/419 |
| 4,810,381 | 3/1989 | Hagen et al. | 210/502.1 |
| 4,824,870 | 4/1989 | Pemawansa et al. | 521/53 |
| 4,855,234 | 8/1989 | Hendrickson et al. | 435/181 |
| 4,868,032 | 9/1989 | Eian et al. | 428/198 |
| 4,871,824 | 10/1989 | Heilmann et al. | 526/304 |
| 4,906,378 | 3/1990 | Hagen et al. | 210/635 |
| 4,914,223 | 4/1990 | Rasmussen et al. | 560/49 |
| 4,950,549 | 8/1990 | Rolando et al. | 428/500 |
| 4,957,943 | 9/1990 | McAllister et al. | 521/64 |
| 4,961,954 | 10/1990 | Goldberg et al. | 427/2 |
| 4,963,494 | 10/1990 | Hibino et al. | 435/288 |
| 4,971,736 | 11/1990 | Hagen et al. | 264/22 |
| 4,979,959 | 12/1990 | Guire | 623/66 |
| 4,981,798 | 1/1991 | Kamakura et al. | 435/179 |
| 4,981,933 | 1/1991 | Fazio et al. | 526/260 |
| 5,006,247 | 4/1991 | Dennison et al. | 210/500.38 |
| 5,013,795 | 5/1991 | Coleman et al. | 525/279 |
| 5,037,656 | 8/1991 | Pitt et al. | 424/443 |
| 5,041,225 | 8/1991 | Norman | 210/500.36 |
| 5,059,654 | 10/1991 | Hou et al. | 525/54.1 |
| 5,071,880 | 12/1991 | Sugo et al. | 521/27 |
| 5,081,197 | 1/1992 | Heilmann et al. | 526/260 |
| 5,155,144 | 10/1992 | Manganaro et al. | 523/134 |
| 5,200,471 | 6/1993 | Coleman et al. | 525/326.9 |
| 5,292,514 | 3/1994 | Capecchi et al. | 424/422 |
| 5,292,840 | 3/1994 | Heilmann et al. | 526/304 |
| 5,328,758 | 7/1994 | Markell et al. | 428/281 |

FOREIGN PATENT DOCUMENTS

| | | | |
|---|---|---|---|
| 32615/68 | 7/1969 | Australia. | |
| 8004587 | 4/1988 | Australia | G01N 33/543 |
| 0264804 | 4/1988 | European Pat. Off. | C12N 11/00 |
| 0336762 | 10/1989 | European Pat. Off. | C08F 8/30 |
| 0392783 | 10/1990 | European Pat. Off. | C08F 255/00 |
| 0392735 | 10/1990 | European Pat. Off. | C08F 8/48 |
| 0407580 | 1/1991 | European Pat. Off. | A61L 33/00 |
| 0443853A2 | 8/1991 | European Pat. Off. | B01J 20/28 |
| 0441660 | 8/1991 | European Pat. Off. | B01D 71/56 |
| 0467639 | 1/1992 | European Pat. Off. | B29C 59/14 |
| 2199946 | 7/1988 | United Kingdom | G01N 33/545 |
| WO90/05018 | 5/1990 | WIPO | B01D 63/02 |
| WO92/07640 | 5/1992 | WIPO | B01D 63/02 |
| WO92/07899 | 5/1992 | WIPO | C08J 7/04 |
| WO93/06925 | 4/1993 | WIPO | B01J 20/28 |

OTHER PUBLICATIONS

Kesting, "Synthetic Polyomeric Membranes: A Structural perspective" 2nd Ed., John Wiley & Sons, pp. 237–286 (1985).

Coleman et al., Journal of Chromatography, "Immobilization of Protein A at high density of azlactone–functional polymeric beads and their use in affinity chromatography", John Wiley, pp. 345–363 (1990).

Shkolnik et al., Journal of Applied Polymer Science, vol. 27, John Wiley, pp. 2189–2196 (1982).

Hsiue et al., Journal of Applied Polymer Science, vol. 30, John Wiley, pp. 1023–1033 (1985).

"Polyazlactones", Encyclopedia of Polymer Science and Engineering, vol. 11, John Wiley, pp. 558–571 (1988).

Richards, John R., "Immobilization of Biomolecules Using Radiation Grafting", Biomedical Engineering Internship Report, University of Minnesota, 1988.

*Primary Examiner*—Peter F. Kulkosky
*Attorney, Agent, or Firm*—Gary L. Griswold; Walter N. Kirn; John H. Hornickel

[57] ABSTRACT

A composite membrane is provided having covalently azlactone functional particles incorporated in a membrane formed by solvent phase inversion. The azlactone functional particles have surfaces of covalently reactive functional groups capable of directly forming covalent chemical bonds with ligands without need for an intermediate activation step. An adduct composite membrane is also provided comprising the membrane and derivatized particles dispersed therein. The derivatized particles comprise a direct, covalent reaction product of ligand with the covalently azlactone functional particles. Methods of making and using the composite membranes and adduct composite membranes are also provided.

10 Claims, No Drawings

AZLACTONE FUNCTIONAL PARTICLES INCORPORATED IN A MEMBRANE FORMED BY SOLVENT PHASE INVERSION

FIELD OF THE INVENTION

The present invention relates to a membrane formed by solvent phase inversion containing azlactone functional particles incorporated therein to form an azlactone composite membrane. The composite article is useful in diagnostic devices, in affinity purifications and enzyme immobilization.

BACKGROUND OF THE INVENTION

Finely divided solids or particles, commonly referred to as fillers, are often added to polymer systems to produce a variety of solid, essentially nonporous, composite materials. Fillers are typically added to polymeric materials for the purposes of either improving physical properties or reducing overall cost. These fillers are primarily inert, unreactive particles, chosen largely according to their compatibility with the matrix polymer and/or their inexpensive nature. Typical of such fillers are minerals, clays, metallic powders, inorganic oxides, glass, talc, wood powder, and carbon black.

Porous, particle-filled composite articles are also known in the art. These materials find use in such applications as filtration or separation media, or in other applications where permeability to gases or liquids is required.

U.S. Pat. No. 4,957,943 describes a microporous particulate-filled thermoplastic polymeric article which may be in the form of a film, a fiber, a hollow fiber, or a tube. The particulate filler is of submicrometer or low micrometer size and may be a metal, a metal oxide, or a carbonaceous material such as carbon black. These composites are useful as protective garments or as X-ray or electromagnetic shielding materials.

U.S. Pat. Nos. 4,550,123 and 4,342,811 describe microporous polymeric fibers and films which contain particles capable of sorbing vapors, liquids, and solutes. Typical sorbent particles include active carbon, silica gel, and molecular filter type materials.

In addition to particulate-filled microporous materials described above, it is also known to incorporate particles into macroporous fibrous webs or sheet materials. For example, U.S. Pat. No. 3,971,373 describes a porous sheet product comprising a web of entangled melt-blown organic polymeric microfibers and a three dimensional array of solid particles uniformly dispersed and physically held in the web. Typical particles are activated carbon or alumina. The composite sheets are useful for adsorbing organic or acidic vapors from an air stream. U.S. Pat. No. 4,963,431 discloses a permeable, nonwoven polymer pad having zeolite particles adhesively bonded throughout the pad. This pad is useful for absorbing ammonia from a fluid.

U.S. Pat. No. 4,153,661 describes a uniformly porous, high void-volume composite sheet comprised of a particle material uniformly distributed throughout a matrix formed of interentangled, fibrillated polytetrafluoroethylene (PTFE) fibrils. The described particles are primarily inorganic particles. U.S. Pat. Nos. 4,373,519 and 4,460,642 describe the incorporation of hydrophilic, organic, water-swellable particles into a fibrillated PTFE matrix. Preferred composites contain particles of crosslinked dextran and are useful as a wound dressing. U.S. Pat. No. 4,810,381 discloses a composite chromatographic article comprising a PTFE fibril matrix and a non-swellable sorptive particle enmeshed in the matrix. Preferred particles are inorganic oxides such as silica and zirconia.

The immobilization of proteins or enzymes on insoluble, solid supports has long been recognized as being desirable. Immobilization allows easy recovery and reuse, and often enhances stability, of biologically active molecules. Methods of immobilization range from physical adsorption, to physical entrapment, to ionic or covalent bonding of the biologically active molecule to the support.

U.S. Pat. No. 4,855,234 discloses a composite article provided by subjecting a fibrous support in sequence to a surface modification treatment, a coating of a protein immobilizer compound, and a biologically active protein. U.S. Pat. No. 4,963,494 describes an ultrafiltration membrane having an enzyme immobilized thereon. Immobilization is accomplished by impregnating a membrane with a solution of a water-soluble polymer, utilizing a crosslinking agent to crosslink the polymer within the pores of the membrane, then covalently binding the enzyme to the membrane through functional groups of the crosslinked polymer.

U.S. Pat. No. 4,102,746 discloses proteins such as enzymes immobilized on a microporous binder or matrix having finely divided filler particles dispersed throughout the binder. Proteins are covalently coupled via a chemical bond to dispersed filler particles in the microporous material, using bridging agents in a two-step procedure.

U.S. Pat. No. 5,041,225 discloses a hydrophilic, semipermeable membrane of PTFE having internal and external surfaces coated with a complex of a hydrophilic polymer which adheres to the membrane structure and a complexing agent. The complex renders the PTFE membrane hydrophilic and protein affinitive. Preferred complexing agents are boric acid, sodium borate, or sodium chloride.

SUMMARY OF THE INVENTION

What the art needs is a composite membrane which combines a membrane, continuous and porous in nature, formed by solvent phase inversion and azlactone functional particles which are directly covalently reactive with ligands, without intermediate activation steps such as those required in U.S. Pat. No. 4,102,746. Such azlactone functional reactive particles incorporated in a membrane formed by solvent phase inversion combine facility of ligand derivatization of such particles in a simplified procedure with substantial assurance of covalent coupling of the ligand on the reactive particles incorporated in the membrane for further chemical or biological interaction.

Briefly, the present invention is a composite membrane formed by solvent phase inversion in the presence of azlactone functional particles that unexpectedly survive the conditions of solvent phase membrane formation to to retain direct, covalent reactivity with ligands without need for an intermediate activation step.

In another aspect, the present invention provides an adduct composite membrane, comprising the composite membrane described above and derivatized particles dispersed therein. The derivatized particles comprise a direct, covalent reaction product of ligand with azlactone functional particles. In a particularly preferred aspect of the present invention, the ligand is a biologically active material. In this aspect, the present invention therefore provides a composite membrane comprising biologically active material covalently immobilized to particles dispersed within the membrane.

The invention provides a composite membrane useful in at least diagnostics devices, in affinity purifications, or in enzyme immobilization.

In another aspect, the invention provides a method for providing a composite membrane described above comprising the steps of providing azlactone functional particles and forming, using solvent phase inversion, a membrane about the azlactone functional particles, wherein the azlactone functional particles retain direct covalent reactivity despite presence during membrane formation.

The method further comprises covalently coupling a ligand to the azlactone functional particles by direct covalent chemical bonds either prior to the membrane-forming process or after the membrane-forming process.

A feature of the present invention is that the composite article has reactive particles dispersed, preferably substantially uniformly, in a continuous, porous matrix which can be directly derivatized with a ligand by covalent coupling.

Another feature of the present invention is that the composite membrane can be rendered biologically active by direct covalent coupling of a biologically active material as a ligand to azlactone functional particles. This direct covalent coupling reduces incidence of biologically active material leaching from or becoming inactive on the azlactone functional particles.

Another feature of the invention is the ability to use a variety of materials for membrane formation via solvent phase inversion, thereby selecting the physical properties desired for the membrane while introducing azlactone functional particles therein.

An advantage of the present invention is that azlactone functional particles of the composite membrane can determine biological or chemical interaction with analytes in a fluid while the continuous, porous matrix enables physical interaction with such analytes in the fluid.

Another advantage of the invention is that azlactone functional particles survive the formation of a membrane in a manner that the particles remain azlactone functional and are not covered by a layer or coating of the polymer(s) constituting the membrane.

EMBODIMENTS OF THE INVENTION

A composite membrane of the present invention is a continuous, porous matrix having dispersed therein directly covalently reactive azlactone functional particles. The particles are directly covalently reactive because azlactone functional groups, capable of forming a covalent chemical bond to a ligand, are present on internal and/or external surfaces thereof.

Azlactone functional particles useful in the present invention can have a spherical shape, a regular shape, or an irregular shape. Size of azlactone functional particles can vary widely within the scope of the invention and will depend to some extent upon the membrane into which such particles are incorporated. Generally size of azlactone functional particles ranges from 0.1 micrometers to 5 millimeters in average diameter.

The azlactone functional groups which are useful for the purposes of the invention can be classified in general as electrophiles. Reaction with a nucleophile (e.g. amine, alcohol, or mercaptan) produces a covalent chemical bond by an addition reaction.

Azlactone functional particles have an azlactone-functional group of Formula I:

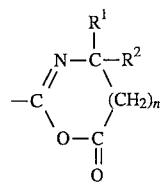

wherein:
$R^1$ and $R^2$ independently can be an alkyl group having 1 to 14 carbon atoms, a cycloalkyl group having 3 to 14 carbon atoms, an aryl group having 5 to 12 ring atoms, an arenyl group having 6 to 26 carbon and 0 to 3 S, N, and nonperoxidic O heteroatoms, or $R^1$ and $R^2$ taken together with the carbon to which they are joined can form a carbocyclic ring containing 4 to 12 ring atoms, and n is an integer 0 or 1.

Azlactone functional particles are used in the present invention because such particles directly covalently couple ligands better than other commercially available reactive functional groups.

Unexpectedly, azlactone functional groups are stable in the presence of solvents used to form the membrane via solvent phase inversion. Further, azlactone functional groups are stable in the presence of water used in the formation of the membrane via solvent phase inversion.

Unexpectedly, azlactone functional groups are exposed on surfaces of the composite membrane formed using solvent phase inversion, such that their functionality is retained and is useful for covalent coupling with a ligand.

Further, such azlactone-functional groups are quite stable prior to covalent coupling with a ligand. Further, covalent coupling of a ligand with an azlactone-functional group causes no displacement of a byproduct molecule, which avoids undesired purification of the composite membrane after covalent coupling of the ligand.

Also, azlactone-functional groups are known to possess high covalent coupling capacities with biologically active materials such as Protein A. Further, such high covalent coupling capacities with Protein A also yield high specific bound biological activity of Protein A as the coupled ligand.

Azlactone-functional polymeric particles can be made, for example, by copolymerization of a (meth)acryloylamino acid with a variety of other free radically polymerizable comonomers followed by reaction with a cyclizing agent, as described in U.S. Pat. Nos. 4,737,560 and 4,871,824, which is incorporated herein by reference, or by copolymerization of an alkenyl azlactone with other comonomers as described in U.S. Pat. No. 5,292,840, which is incorporated by reference herein. Azlactone-functional particles can also be prepared by solution coating an azlactone-functional polymer onto an organic or inorganic particle, also as described in above mentioned U.S. Pat. No. 5,292,840.

Azlactone-functional particles can also be made from azlactone graft copolymers which are disclosed in U.S. Pat. Nos. 5,013,795 and 5,262,484, which are incorporated herein by reference.

Azlactone-functional particles can also be made by graft polymerization onto base supports which contain aliphatic hydroxyl groups on their surfaces as described in European Patent Publication 0 565 978, the disclosure of which is incorporated by reference.

Size of particles of azlactone-functional particles can be from about 0.1 to 1,000 micrometers and preferably from 0.5 to 100 micrometers. Azlactone-functional particles can be porous or non-porous. When porous, the average pore size of the dry azlactone-functional particles can range from about 1 to about 3,000 Angstroms and preferably from 10 to about 500 Angstroms.

Azlactone-functional particles are commercially available in one embodiment as Emphaze™AB 1 beads, commercially available from 3M Bioapplications, Minnesota Mining and Manufacturing Company, St. Paul, Minn.

Membrane Composition

Membrane compositions can be any compound capable of forming a membrane in a solvent phase inversion process.

Solvent phase inversion is a conventional process for making microporous membranes, having effective pore sizes ranging from about 0.05 to about 50 µm, and preferably from about 0.1 to about 10 µm, when used to separate cells, cell fragments, and the like. Solvent phase inversion involves the making of a solution of the polymer to become the membrane, forming the dissolved polymer into a desired shape, and exposing the solution to a non-solvent of the polymer to cause the polymer to precipitate from solution and form a membrane in the desired shape. Conventional solvent phase inversion techniques are disclosed in Kesting, "Synthetic Polymeric Membranes. A Structural Perspective" 2nd Ed., John Wiley and Sons, 1985, the disclosure of which is incorporated by reference herein. In the case of nylon membranes, one skilled in the art can refer to U.S. Pat. No. 5,006,247, the disclosure of which is incorporated by reference herein.

Optional other polymers and a variety of additives that also dissolve into the solvent can be added as known to those skilled in the art.

Commercially available compositions are useful for formation of membranes using solvent phase inversion. The composite membrane of the present invention achieves the advantages of the membrane formed using the conventional solvent phase inversion techniques plus the unexpected advantage of introducing directly covalently reactive azlactone-functional particles during the formation of the membrane with the survival of azlactone-functionality in the composite membrane for ligand derivatization of the composite membrane.

Nonlimiting examples of compositions useful in the formation of membranes for the present invention include cellulose acetate, polysulfones, poly(ethersulfones), poly(vinylidene fluoride), poly(acrylonitrile), poly(vinyl acetate), poly(vinyl chloride), cellulose nitrate, ethylene vinyl acetate, and nylons, and combinations thereof, and poly(N-vinyl lactams) in combination with the above polymers.

Incorporation of Azlactone-functional Particles into the Membrane

The amount of azlactone functional particles incorporated into the membrane can vary widely within the scope of the present invention, within some limitations. Some of the casting solvents used in forming the membrane could detrimentally affect azlactone functionality of the particles. Also, in some membranes, high loadings of azlactone functional particles could degrade the physical properties of the membrane formed about the particles.

Generally, the amount of azlactone functional particle can range from about 1 to about 50% by mass of the material comprising the composite membrane. Preferably, the amount is about 5 to about 20% by mass, and more preferably about 10 to about 20% by mass.

As indicated above, the size of azlactone functional particles can vary from about 0.1 micrometer to 5 millimeters in average diameter. Preferred size ranges, however, depend upon the thickness and shape of membrane in which azlactone functional particles are incorporated. For composite membranes, much smaller particles, in the range of 0.1 to 20 micrometers, preferably 0.5 to 3 micrometers, and most preferably 0.5 to 1 micrometer, are useful. Ultimately, differences in useful particle sizes are dictated by the processes and equipment which are utilized to form the membrane and the porosity of the membrane so formed.

In addition, certain adjuvants may be added to the composite membranes of the present invention to include nonazlactone functional particles and fillers, processing aids, surfactants, and the like. The desirability and methods of incorporation of such adjuvants into a continuous, porous matrix is described in greater detail in the above referenced and incorporated patents describing formation of matrices useful for the present invention.

Composite Membrane Formation from Polymer Solutions

Composite membranes are formed from polymer solutions, with or without blending polymers, whether or not the polymer was polymerized from monomers in the solvent or was polymerized prior to dissolution in the solvent.

Solvents used for membrane formation can be at least one solvent both (1) capable of dissolving all membrane-forming compositions and (2) miscible with the coagulating bath employed for solvent phase inversion. Desirably, the solvent is a polar organic solvent that can dissolve membrane-forming polymers and optional blending polymers. Nonlimiting examples of such polar organic solvents are amides, (e.g, dimethylacetamide (DMAC) and dimethylformamide (DMF)), ketones, (e.g., methyl ethyl ketone (MEK)); furans, (e.g., tetrahydrofuran (THF)), and alcohols with chloride salts (e.g., methanol and $CaCl_2$) when nylons are involved, or mixtures thereof. Preferably, the solvent is DMAC for non-nylon membranes and a 65/35 mixture of methanol and $CaCl_2$ for nylon membranes.

Composite membrane formation in the solvent is based on the amount of polymer solids dissolved and the amount of azlactone functional particles dispersed in the solvent. The amount of solids dissolved must be high enough to be able to be cast onto a substrate without being too high, which will form a membrane with little porosity. On the other hand, the amount of solids dissolved must not be too low, as it will fail to achieve the formation of a membrane. The total weight percent solids of all polymers used to form the membrane depends on the type and molecular weight of the polymer(s) in the coating solution and acceptably can range from about 5 to about 40. Desirably, the total weight percent solids of all polymers used to form the membrane can range from about 10 to about 30 because a good membrane thickness is obtained. Preferably, the total weight percent solids of all polymers used to form the membrane can range from about 15 to about 25 because a preferred porosity membrane can be obtained.

Reaction conditions for the formation of membranes by solvent phase inversion technique follows procedures known to those skilled in the art, particularly when applying Kesting as described above. However, formation of composite membranes of the present invention adds azlactone functional particles prior to membrane formation wherein the azlactone functionality of the particles survive both the solvents used to dissolve the compositions used to form the membranes and the coagulation bath.

In this invention, to assist dissolution of any solids introduced into the reaction vessel, the reaction vessel can be heated to about 70° C. Otherwise, the solution formation is carried out at ambient conditions. The solution is cast onto a surface and the solvent can be partially evaporated for about 15–20 seconds in order to control porosity of the resulting membrane.

The thickness of the casting is important. Using a casting knife, the casted solution can not be too thick because coagulation is not rapid enough and can not be too thin because structural integrity of the resulting membrane will be reduced. Generally, the membrane thickness is about the same thickness as the coating and one-half of the gap of the casting knife. Thus, the casting should be about 0.05 mm to about 1 mm, and desirably from about 0.1 mm to about 0.4 mm thick. To achieve the above thicknesses, the casting knife should have a gap of about 100 μm to about 2 mm, desirably from about 200 μm to 800 μm, and preferably about 250 μm, respectively.

The casting on the substrate is then immersed in a coagulating bath for a time from about 1 min. to about 30 min. to permit the casting to form a composite membrane with azlactone functional particles dispersed therein. The coagulating bath can be water, ethanol, or another polar solvent, or a mixture of solvents to provide a pH of the liquids in the reaction vessel of about 6–8 and preferably from about 6.5 to 7.5. Desirably, the coagulating bath also contains a small amount, about 10 volume percent, of an organic solvent, such as methanol, ethanol, DMAC, DMF, and the like. Preferably the coagulation bath is pure water.

Coagulation conditions are temperatures ranging from about 0° C. to about 70° C., desirably ranging from about 10° C. to 50° C., and preferably about 20° C. to 30° C. with slight to moderate agitation as desired.

After formation of the composite membrane in the coagulating bath, the membrane is removed, dried as required, and stored in a aridity controlled environment to assure the dried composite membrane remains dry.

The composite membrane formation process can be a batch process or a continuous process according to techniques known to those skilled in the art. An advantage of the membrane formation process is that no subsequent processing steps are required in the formation of the membrane; it is azlactone-functional and remains azlactone-functional until ready for use.

Sizes (length and width) of the composite membranes formed can be controlled by the size of the batch or continuous processing equipment as known to those skilled in the art. Also, membrane sizes can be reduced by cutting the composite membranes to desired two-dimensional areas using dies, slitting knives, or the like.

As an alternative embodiment to the formation of the composite membrane, a composite membrane having adduct particles dispersed therein can be formed by including a desired ligand in the coagulation bath. As the membrane forms in the coagulation bath, reaction with one or more azlactone moieties in the particles dispersed in the membrane with the ligand forms the adduct composite membrane.

Adduct Composite Membranes and Usefulness of the Invention

Because azlactone-functional particles dispersed in a membrane formed by solvent phase inversion are capable of multiple chemical reactions, azlactone-functional modified surfaces of the present invention can form adduct-functional membranes after formation and storage of the membrane.

Electrophilic azlactone-functional moieties in the composite membrane can react through a nucleophilic ring opening reaction at the carbonyl group with any of a myriad of nucleophilic reagents. The result is the formation of an adduct composite membrane having specific reactivities determined by the nature of the nucleophilic reagent employed in the reaction.

Nonlimiting examples of nucleophilic reagents include biologically active substances, acids, bases, chelators, hydrophiles, lipophiles, hydrophobes, zwitterions, detergents, and any other chemical which can react with the azlactone-functionality on the surfaces of the membrane a modified reactivity. For example, one can modify a hydrophobic surface by reacting an azlactone-functional adduct support with a nucleophilic, hydrophilic moiety. Examples of nucleophilic, hydrophilic compounds include poly(ethylene oxide) commercially available as Jeffamines from Texaco, Inc.

Ligands and Adduct Membranes

Adduct membranes have ligands coupled or otherwise tightly bound to azlactone-functional particles dispersed in the composite membranes to form biologically or chemically active reaction sites. For direct coupling, nonlimiting examples of nucleophilic ligands include primary and secondary amines, alcohols, and mercaptans. Of these, amine-functional ligands are especially preferred.

While not being limited to a particular theory, it is believed that a ligand forms a covalent bond when coupled to an azlactone-functional moiety.

Ligands useful for the preparation of adduct supports can also vary widely within the scope of the present invention. Preferably, a ligand is chosen based upon the contemplated end use of the adduct support.

Once ligands are coupled to azlactone-functional grafts or coatings, such ligands are available for biological or chemical interaction, such as adsorbing, complexing, catalysis, or reagent end use.

Adduct composite membranes are useful as adsorbants, complexing agents, catalysts, reagents, as enzyme and other protein-bearing supports, and as chromatographic articles.

In a preferred aspect of the present invention, the ligand desired for coupling is a biologically active substance having azlactone-reactive, nucleophilic-functional groups. Nonlimiting examples of biologically active substances are substances which are biologically, immunochemically, physiologically, or pharmaceutically active. Examples of biologically active substances include proteins, peptides, polypeptides, antibodies, antigenic substances, enzymes, cofactors, inhibitors, lectins, hormones, receptors, coagulation factors, amino acids, histones, vitamins, drugs, cell surface markers, and substances which interact with them.

Of the biologically active substances, proteins, enzymes and antigenic substances are desired for coupling to azlactone-functional supports. Nonlimiting examples of proteins, enzymes, and antigenic substances include natural and recombinant Protein A (ProtA), Immunoglobulins such as rat (rIgG), human (hIgG), bovine (bIgG), rabbit (rbIgG), and mouse (mIgG), Concanavalin A (ConA), Bovine Serum Albumin (BSA), Thyroglobulin (TG), Apoferritin (Af), Lysozyme (Ly), Carbonic Anhydrase (CA), Lipase, Pig Liver Esterase, Penicillin acylase, and Bacterial Antigen (BA). Uses for immobilized proteins, enzymes and antigenic substances are disclosed in U.S. Pat. No. 5,292,840.

Alternatively, an adduct composite membrane of the present invention can comprise a coupled enzyme to catalyze a chemical transformation of substances recognized by the enzyme. Also, a membrane comprising a coupled antigenic substance can be utilized for affinity purification of a corresponding antibody from a complex biological fluid flowing through the porous membrane. In other examples, an adduct membrane having Protein A coupled to particles dispersed therein can adsorb biologically active materials such as Immunoglobulin G for affinity separations processes. In other examples, an adduct support can be used for immobilization of antibodies or be used for immunodiagnostics or for Western blotting.

Alternatively, the ligand can be a hydrophile for improving compatibility of mammalian body implants, such as intraocular lenses, with adjoining tissues. One example of a ligand especially suitable for chemically modifying body implants is an anticoagulant, such as a chemically-modified heparin, e.g., an amine-terminated heparin.

Azlactone-functional moieties will undergo nucleophilic attack by amines, thiols, and alcohols. Thus, ligands having at least one amine, thiol, or alcohol group thereon are candidates for coupling to azlactone-functional surfaces. Amine-functional ligands are preferred due to ease of reaction and stability of the linkage so formed.

Coupling of ligands to preferred azlactone-functional surfaces can use methods of using inorganic or organic polyanionic salts in such concentrations as to achieve high broad specific biological activity for the coupled ligand, such as methods disclosed in U.S. Pat. No. 5,200,471 (Coleman et al.), the disclosure of which is incorporated by reference.

Coupling of ligands to azlactone-functional particles according to the present invention results in adduct supports having the formula

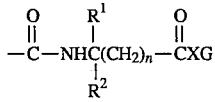

wherein
R$^1$, R$^2$, and n are as previously defined, R$^3$ is H or CH$_3$,
X can be —O—, —S—, —NH—, or —NR$^4$ wherein R$^4$ can be alkyl or aryl, and
G is the residue of HXG which performs the adsorbing, complexing, catalyzing, separating, or reagent function of the adduct support.
HXG is a nucleophilic reagent and can be a biologically active material, dye, catalyst, reagent, and the like.

Ligands having azlactone-reactive, amine, hydroxy, or thiol nucleophilic functional groups react, either in the presence or absence of suitable catalysts, with azlactone-functional groups by nucleophilic addition as depicted in the equation.

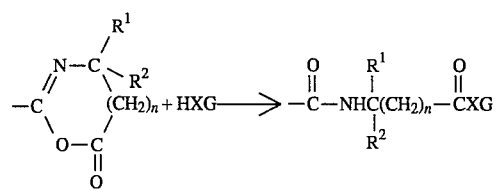

wherein
R$^1$, R$^2$, n, X, and G are as previously defined.

Depending on the functional group present in the ligand, catalysts may be required to achieve effective attaching reaction rates. Primary amine functional groups require no catalysts. Acid catalysts such as trifluoroacetic acid, ethanesulfonic acid, toluenesulfonic acid, and the like are effective with hydroxy and secondary amine functional groups.

In other aspects of the invention, the ligand is not biologically active but has other properties which lead to its end use. For example, the ligand can contain ionic functional groups. In that event, the resultant adduct article may be utilized in ion exchange type applications. Suitable ionic groups include carboxylic acid, sulfonic acid, phosphonic acid, tertiary amine, and quaternary amine groups. Examples of useful ionic group containing ligands include aminocarboxylic, sulfonic, or phosphonic acids such as glycine, alanine, leucine, valine, β-alanine, γ-aminobutyric acid, 1- and 3-aminopropylphosphonic acid, taurine, γ-amino octanoic acid, aminomethylphosphonic acid, amino-methanesulfonic acid, and the like; hydroxy-acids such as isethionic acid, 3-hydroxy-propane sulfonic acid, lactic acid, glycolic acid, hydroxymethylphosphonic acid, p-hydroxybenzoic acid, and the like; and amino- and hydroxy-functional tertiary and quarternary amines such as 2-diethylaminoethylamine, 3-dimethyl-aminopropylamine, N,N-diethylethanolamine, and the like, and quaternized versions thereof. When the amine-, hydroxy- or thiol-functional ligand is a simple aliphatic and/or aromatic hydrocarbon, the resultant adduct composite membrane may be useful in reverse phase or hydrophobic interaction type chromatographic processes. Reaction of the composite membrane of this invention with very hydrophilic or hydrophobic ligands can be used to produce adduct composite membranes displaying highly absorbant properties towards aqueous or oily fluids, respectively. Other types of ligands and uses will be obvious to one skilled in the art and are considered to be within the scope of the present invention.

Composite membranes of the present invention, whether alzactone-functional or adduct, can be used singularly, multiply, or sequentially. When used multiply, stacks of membranes can have the same or different reactivity depending on the type of separation desired. When used sequentially, an array of membranes can have the same or different reactivity depending on the type of separation desired.

Chemically-reactive filtration devices can use composite membranes of the present invention to provide affinity separation of nucleophilic reagents from a fluid stream.

Objects and advantages of this invention are further illustrated by the following examples, but the particular materials and amounts thereof recited in these examples, as well as other conditions and details, should not be construed to unduly limit this invention.

EXAMPLES

Protein Testing Procedure

Protein solutions were radiolabeled using Iodo-Beads™ beads (commercially available from Pierce Chem., Rockford, Ill.) and NaI-125 (Dupont NEN, Billerica, Mass.) using the procedures described in the product insert. Specific radioactivities obtained were: Protein A, (Genzyme, Boston) 2782 cpm/µg; immunoglobulin G (IgG, Sigma Chem., St. Louis), 2000 cpm/µg; and bovine serum albumin (BSA, Sigma), 2885 cpm/µg.

Circular portions (7 mm diameter) of the membrane were cut out using a paper punch. The membrane discs were then incubated with radiolabeled protein in 250 µl of 250 mM sodium phosphate, 1.5M sodium sulfate, pH 7.5, for 60 min. at ambient temperature. Following the protein incubations all membranes were reacted an additional 15 min. with 500 µl of 3.0M ethanolamine, pH 9.0, to inactivate remaining azlactones as well as rinse out unbound protein. Each membrane was subsequently rinsed an additional three times with 500 µl of the phosphate buffer. After the bound radioactivity was determined using a Model 5230 Auto-Gamma scintillation counter (Packard, Downers Grove, Ill.), the membranes were incubated for 4 h at 37° C. in 500 µl of 1.0% sodium dodecylsulfate (SDS) solution followed by determination of residual radioactivity. SDS is a strongly denaturing detergent capable of removing all but the most tenaciously bound protein. In these experiments, control membranes were completely untreated. These and all experiments described in this example were performed in triplicate.

Examples 1 and 2

A solution was made by dissolving 2 g of cellulose acetate (available from Eastman Kodak as CA 389-30) in 8 g N,N-dimethyl acetamide. To 2 g of this solution were added 0.02 g of azlactone beads prepared according to Example 24E of U.S. Pat. No. 5,292,840. The mixture was briefly stirred with a spatula. The bead mixture was cast on a clean glass plate using a knife coater with a 250 µm gap and immediately placed in a bath of pure water at room temperature. The membrane was allowed to stay in the water bath for about 10 minutes, then removed and dried overnight laying flat at room temperature and room air. The resulting membrane was examined by scanning electron microscopy and was found to have a homogeneous porous structure with the azlactone beads distributed throughout.

A second membrane was made in the same manner as Example 1, except that poly(vinylidene fluoride), (commercially available as Solef 5008 from Solvay Polymer Corporation of Houston, Tex.) was used in place of cellulose acetate.

The membranes were tested for protein binding and several physical properties were evaluated. The bead-containing cellulose acetate membrane was found to bind 4.8 µg of Protein A per $cm^2$ of membrane, with an SDS resistance of 45%. The bead-containing poly(vinylidene fluoride) membrane was found to bind 119.9 µg of Protein A per $cm^2$ of membrane, with an SDS resistance of 33%. These membranes demonstrated the feasibility of the present invention, in that azlactone functionality survived the membrane formation process using solvent phase inversion and survived on the surfaces of the membrane to couple with Protein A.

Example 3 and Comparison Example A

A solution was made by adding 10 g of polysulfone (UDEL P3500, Union Carbide) and 10 g of polyvinyl pyrrolidone (Plasdone K90, GAF) to 80 g of N,N-dimethylacetamide and shaking until the polymers were dissolved. 5 g of the solution were weighed out and 0.2 g of azlactone beads prepared according to Example 24E of U.S. Pat. No. 5,292,840, were added by mixing with a spatula. The bead-containing solution was spread on a glass plate using a knife coater with a 250 µm clearance, it was allowed to evaporate for 15 seconds, and then placed in a pure water bath for about 30 minutes. The membrane was then removed from the glass plate and dried under nitrogen. A second membrane was made using identical conditions except no beads were added.

The membranes were tested for protein binding and several physical properties were evaluated. The bead-containing membrane was found to bind 49.4 µg of Protein A per $cm^2$ of membrane, with an SDS resistance of 92.6%. By contrast, the membrane with no beads bound 2.9 µg of Protein A with an SDS resistance of 41.3%. The measured physical properties of the two membranes were quite similar, with basis weights of 49 and 42 $g/cm^2$ and porosities of 60 and 61% respectively. Both membranes were water wettable.

Examples 5–12 and Comparison Examples B–E

A number of membranes (Examples 5–10 and Comparison Examples B–D) were made following the same procedure as used in Example 3 and tested for protein binding.

The other membranes (Examples 11–12 and Comparison Example E) were made using a nylon solution made as described in Example 26, U.S. Pat. No. 5,006,247, the disclosure of which is incorporated by reference herein. Briefly, 35 grams of calcium chloride dihydrate was added to 60 grams of methanol and the mixture was held at reflux for 2 to 3 hours until the salt was dissolved. 5 grams of nylon 6,6 (Celanese 1200-1 commercially available from Hoeschst-Celanese) was added to the solution and held at reflux for about 12 hours until the polymer was dissolved and a clear, casting solution was obtained. Azlactone functional beads were the same as used in Example 3.

The contents of the casting dopes are given in Table 1 and the characterization results are given in Table 2. As can be seen, adding the azlactone beads in all cases increased the total amount of protein bound as well as the amount of protein resistant to SDS wash. The amounts of these increases and the absolute magnitudes of protein bound vary considerably from membrane to membrane, and probably depend on both the interactions of the beads with the polymer and, especially in the case of the nylon membranes, the effect of the casting solvent on the beads.

TABLE 1

| Example Number | Polymer | Solvent | % Solids | Bead Loading (g/g polymer) |
|---|---|---|---|---|
| 5 | Polyvinylpyrrolidone/ Polysulfone (50/50) | DMAC | 20 | 0.2 |
| 6 | Polyvinylpyrrolidone/ Polysulfone (50/50) | DMAC | 20 | 0.1 |

TABLE 1-continued

| Example Number | Polymer | Solvent | % Solids | Bead Loading (g/g polymer) |
|---|---|---|---|---|
| B | Polyvinylpyrrolidone/ Polysulfone (50/50) | DMAC | 20 | NO BEADS |
| 7 | Polysulfone | DMAC | 20 | 0.2 |
| 8 | Polysulfone | DMAC | 20 | 0.1 |
| C | Polysulfone | DMAC | 20 | NO BEADS |
| 9 | Cellulose Acetate | DMAC | 20 | 0.2 |
| 10 | Cellulose Acetate | DMAC | 20 | 0.1 |
| D | Cellulose Acetate | DMAC | 20 | NO BEADS |
| 11 | Nylon 66 | Methanol/ CACl$_2$ (65/35) | 5 | 0.2 |
| 12 | Nylon 66 | Methanol/ CACl$_2$ (65/35) | 5 | 0.1 |
| E | Nylon 66 | Methanol/ CACl$_2$ (65/35) | 5 | NO BEADS |

Table 1. Legend
Casting dopes used to make azlactone particle-containing membranes. DMAC is N, N-dimethylacetamide. The polymers and sources are as follows:
Polyvinylpyrrolidone: Plasdone K90, GAF
Polysulfone: UDEL P3500 NJ, Union Carbide
Cellulose Acetate: CA 398-30, Eastman Kodak
Nylon 66: Celanese 1200-1, Hoechst-Celanese

TABLE 2

| Example Number | Membrane | Bead Loading (g/g polymer) | Basis Wt. g/m$^2$ | Thickness μm | Density g/cm$^3$ | Water Wettable | Porosity % Void | μg pA/cm$^2$ SO$_4$ Buffer | % SDSR SO$_4$ Buffer |
|---|---|---|---|---|---|---|---|---|---|
| 5 | PNVP/PSF | 0.2 | 45.9 | 147 | 0.31 | YES | 69 | 49.4 | 92.6 |
| 6 | PNVP/PSF | 0.1 | 33.3 | 135 | 0.25 | YES | 75 | 21.6 | 91.3 |
| B | PNVP/PSF | NO BEADS | 41.6 | 107 | 0.39 | YES | 61 | 2.9 | 41.3 |
| 7 | PSF | 0.2 | 52.0 | 140 | 0.37 | NO | 63 | 13.5 | 72.9 |
| 8 | PSF | 0.1 | 49.7 | 140 | 0.36 | NO | 64 | 10.3 | 62.4 |
| C | PSF | NO BEADS | 41.6 | 107 | 0.39 | NO | 61 | 7.3 | 54.1 |
| 9 | C.A. | 0.2 | — | — | — | NO | — | 2.0 | 63.0 |
| 10 | C.A. | 0.1 | — | — | — | NO | — | 3.1 | 65.8 |
| D | C.A. | NO BEADS | 30.8 | 127 | 0.24 | NO | 76 | 0.9 | 4.9 |
| 11 | Nylon 66 | 0.2 | 13.9 | 86 | 0.16 | YES | 84 | 2.5 | 42.2 |
| 12 | Nylon 66 | 0.1 | 11.8 | 66 | 0.18 | YES | 82 | 1.6 | 55.9 |
| E | Nylon 66 | NO BEADS | 11.1 | 114 | 0.09 | YES | 99 | 1.4 | 17.5 |

Table 2. Legend
Results of characterization of membranes listed in Table 1.

Examples 13–20 and Comparison Examples F–I

Membranes were made using the procedure used in Examples 5–12, except that the beads used were prepared using Example 25D of U.S. Pat. No. 5,292,840. The casting dopes used are described in Table 3, and the protein binding results are described in Table 4. As can be seen, these membranes bind large amounts of protein with fairly high SDS resistance.

In comparison with the membranes of Examples 5–12, which used more hydrophilic beads, in general the total binding was higher for these hydrophobic beads of Examples 13–20, but in some cases the SDS resistance was slightly lower. These differences were dependent on the casting dope used, and were most significant for the cellulose acetate and nylon membranes, which showed fairly low binding with the hydrophilic beads of Examples 5–12. For these two membranes, both the total amount bound and the SDS resistance were higher when the hydrophobic beads were used.

This suggested the choice of the specific azlactone bead to use could depend on the nature of the membrane casting solution being used, as well as the proposed use of the composite membrane. For example, a more hydrophobic bead could tolerate the presence of hydroxyl groups in the casting solution (as is the case with the nylon and cellulose acetate membranes) better than more hydrophilic beads.

TABLE 3

| Example Number | Polymer | Solvent | % Solids | Bead Loading (g/g polymer) |
|---|---|---|---|---|
| 13 | Polyvinylpyrrolidone/ Polysulfone (50/50) | DMAC | 20 | 0.2 |
| 14 | Polyvinylpyrrolidone/ Polysulfone (50/50) | DMAC | 20 | 0.05 |
| F | Polyvinylpyrrolidone/ Polysulfone (50/50) | DMAC | 20 | NO BEADS |

TABLE 3-continued

| Example Number | Polymer | Solvent | % Solids | Bead Loading (g/g polymer) |
|---|---|---|---|---|
| 15 | Polysulfone | DMAC | 20 | 0.2 |
| 16 | Polysulfone | DMAC | 20 | 0.05 |
| G | Polysulfone | DMAC | 20 | NO BEADS |
| 17 | Cellulose Acetate | DMAC | 20 | 0.2 |
| 18 | Cellulose Acetate | DMAC | 20 | 0.05 |
| H | Cellulose Acetate | DMAC | 20 | NO BEADS |
| 19 | Nylon 66 | Methanol/CACl$_2$ (65/35) | 5 | 0.2 |
| 20 | Nylon 66 | Methanol/CACl$_2$ (65/35) | 5 | 0.05 |
| I | Nylon 66 | Methanol/CACl$_2$ (65/35) | 5 | NO BEADS |

Table 3. Legand
Casting dopes used to make azlactone particle-containing membranes. DMAC is N, N-dimethylacetamide. The polymers and sources are as follows:
Polyvinylpyrrolidone: Plasdone K90, GAF
Polysulfone: UDEL P3500 NJ, Union Carbide
Cellulose Acetate: CA 398-30, Eastman Kodak
Nylon 66: Celanese 1200-1, Hoechst-Celanese

TABLE 4

| Example Number | Membrane | Bead Loading (g/g polymer) | μg pA/cm$^2$ SO$_4$ Buffer | % SDSR SO$_4$ Buffer |
|---|---|---|---|---|
| 13 | Polyvinylpyrrolidone/Polysulfone (50/50) | 0.2 | 100.8 | 60.3 |
| 14 | Polyvinylpyrrolidone/Polysulfone (50/50) | 0.05 | 78.1 | 29.3 |
| F | Polyvinylpyrrolidone/Polysulfone (50/50) | NO BEADS | 48.2 | 11.2 |
| 15 | Polysulfone | 0.2 | 54.0 | 43.9 |
| 16 | Polysulfone | 0.05 | 29.4 | 48.3 |
| G | Polysulfone | NO BEADS | 21.7 | 60.1 |
| 17 | Cellulose Acetate | 0.2 | 27.8 | 82.4 |
| 18 | Cellulose Acetate | 0.05 | 5.9 | 60.5 |
| H | Cellulose Acetate | NO BEADS | 2.8 | 31.6 |
| 19 | Nylon 66 | 0.2 | 45.7 | 70.9 |
| 20 | Nylon 66 | 0.05 | 20.0 | 51.6 |
| I | Nylon 66 | NO BEADS | 12.7 | 24.0 |

Table 4. Legend
Results of Protein A binding to membranes containing hydrophobic beads. All membranes were prewet with isopropanol prior to testing, and all protein binding was done using the sulfate buffer.

Various modifications and alterations of this invention will become apparent to those skilled in the art without departing from the scope and spirit of this invention. It should be understood that this invention is not to be unduly limited to the illustrative embodiments set forth herein.

What is claimed is:

1. A composite membrane comprising:
azlactone functional particles incorporated within a membrane formed by solvent phase inversion, wherein said azlactone functional particles survive formation of the membrane to remain directly covalently reactive with ligands, wherein the membrane is a polymer comprising cellulose acetate, a polysulfone, a poly(ethersulfone), poly(vinylidene fluoride), poly(acrylonitrile), poly(vinyl acetate), poly(vinyl chloride), cellulose nitrate, ethylene vinyl acetate, and nylons, or combinations thereof, or a poly(N-vinyl lactam) in combination with at least one of the polymers.

2. The composite membrane according to claim 1, wherein said azlactone functional particles are reacted with said ligands.

3. The composite membrane according to claim 1, wherein said azlactone functional particles comprise azlactone functional groups having the formula:

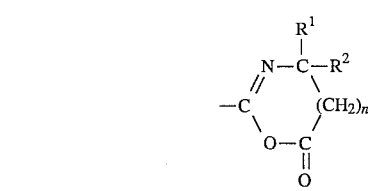

wherein $R^1$ and $R^2$ independently can be an alkyl group having 1 to 14 carbon atoms, a cycloalkyl group having 3 to 14 carbon atoms, an aryl group having 5 to 12 ring atoms, an arenyl group having 6 to 26 carbon and 0 to 3 S, N, and nonperoxidic O heteroatoms, or $R^1$ and $R^2$ taken together with the carbon to which they are joined can form a carbocyclic ring containing 4 to 12 ring atoms, and n is an integer 0 or 1.

4. The composite membrane according to claim 3, wherein said azlactone-functional group is contained in a coating on an inorganic particle or is present on surfaces of particles comprising copolymers including said azlactone-functional group.

5. The composite membrane according to claim 4, wherein said azlactone functional particles have a size ranging from about 0.1 to about 1000 micrometers; wherein said azlactone functional particles are porous; and wherein said reactive functional group covalently couples ligands.

6. The composite membrane according to claim 5, wherein said ligand is selected from the group consisting of biologically active materials and ionically functional materials.

7. The composite membrane according to claim 6, wherein said biologically active material comprises substances which are biologically, immunochemically, physiologically, or pharmaceutically active, and wherein said biologically active material comprises proteins, peptides, polypeptides, antibodies, antigenic substances, enzymes, cofactors, inhibitors, lectins, hormones, receptors, coagulation factors, amino acids, histones, vitamins, drugs, cell surface markers, or substances which interact with them.

8. A method of forming a composite membrane of claim 1, comprising the steps of:

(a) dissolving polymer useful for the preparation of a membrane in a solvent to form a polymer solution;

(b) dispersing azlactone functional particles in the polymer solution;

(c) forming a membrane from the polymer with azlactone functional particles incorporated therein using solvent phase inversion.

9. The method according to claim 8, wherein said azlactone functional particles are reacted with ligand prior to said dispersing step to form an adduct composite membrane.

10. The method according to claim 8, further comprising the step (d) of reacting said azlactone functional particles with ligand after said forming step to form an adduct composite membrane.

\* \* \* \* \*